United States Patent [19]

Agran

[11] Patent Number: 5,059,181
[45] Date of Patent: Oct. 22, 1991

[54] NON-RECHARGEABLE DISPOSABLE SYRINGE

[76] Inventor: Robert B. Agran, 909 Quantril Way, Baltimore, Md. 21205

[21] Appl. No.: 474,544

[22] Filed: Feb. 2, 1990

[51] Int. Cl.⁵ ............................................. A61M 5/00
[52] U.S. Cl. .................................. 604/110; 604/210; 604/220; 128/919
[58] Field of Search ................ 128/919; 604/110, 187, 604/209, 210, 218, 220, 221, 224, 227

[56] References Cited

U.S. PATENT DOCUMENTS

| | | | |
|---|---|---|---|
| 4,826,483 | 5/1989 | Molnar | 604/110 |
| 4,878,899 | 11/1989 | Plouff | 604/110 |
| 4,887,999 | 12/1989 | Alles | 604/110 |
| 4,906,231 | 3/1990 | Young | 604/110 |
| 4,932,941 | 6/1990 | Min et al. | 604/110 |
| 4,973,310 | 11/1990 | Kosinski | 604/110 |
| 4,978,339 | 12/1990 | Labouze et al. | 604/110 |
| 4,995,869 | 2/1991 | McCarthy | 604/110 |
| 5,021,047 | 6/1991 | Movern | 604/110 |

FOREIGN PATENT DOCUMENTS

| | | | |
|---|---|---|---|
| 0340899 | 11/1989 | European Pat. Off. | 604/110 |
| 2184657 | 7/1987 | United Kingdom | 604/110 |
| 8900432 | 1/1989 | World Int. Prop. O. | 604/110 |
| 8902287 | 3/1989 | World Int. Prop. O. | 604/110 |

*Primary Examiner*—C. Fred Rosenbaum
*Assistant Examiner*—Mark O. Polutta
*Attorney, Agent, or Firm*—Leonard Bloom

[57] ABSTRACT

A non-rechargeable, disposable hypodermic syringe for use with a needle includes a barrel, a retaining ring, and a plunger. The plunger has at least one annular notch formed therein. The barrel has at least one internal inwardly-flared tab formed therein which is oriented towards the forward end of the barrel. The tab is inwardly-biased, so that during rearward movement of the plunger, after delivery of the substance therein, the tab is received in the notch for annularly engaging in the notch, preventing the plunger's continued rearward movement and preventing the recharging of the syringe. In this manner, the syringe cannot be reused. The retaining ring is circumferentially disposed in the barrel between the plunger and the barrel. Cooperating ratchet teeth between the plunger and the ring coordinate the forward movement of the plunger with the ring, permitting the initial filling and aspiration of the syringe.

30 Claims, 5 Drawing Sheets

FIG.10D FINAL POSITION (NON-RETRACTABLE)

FIG.10C INJECTING POSITION

FIG.10B LOADING POSITION

FIG.10A INITIAL POSITION

NON-RECHARGEABLE DISPOSABLE SYRINGE

FIELD OF THE INVENTION

The present invention relates to disposable syringes and, in particular, to disposable syringes that are non-rechargeable.

BACKGROUND OF THE INVENTION

The use of hypodermic syringes for the delivery of a variety of substances is well known. Most commonly, syringes are used in the administration of medication to the sick as well as to immunize against certain communicable diseases. Once used, the syringe is then discarded.

Unfortunately, common hypodermic syringes remain rechargeable (and hence reusable) even after their initial intended use. Thus, once the delivery of the intended substance is complete, the syringe can be utilized again. This is undesirable in that such reuse can result in infection and/or in the spread of communicable disease. In recent years, this problem has been amplified by the emergence of AIDS as a health hazard, which has, at least in part, been spread by the sharing (reuse) of such "dirty" syringes, including syringes which have been discarded, by drug abusers.

In order to alleviate such disposal problems, a number of syringes have been disclosed which are designed to be non-rechargeable, in order to prevent the reuse thereof. Such syringes, of which I am aware, are as follows:

| Inventor | Patent No. | Year Of Issue |
| --- | --- | --- |
| Solowey | 3,478,937 | 1969 |
| Legendre et al. | 4,367,738 | 1983 |
| Butterfield | 4,493,703 | 1985 |
| Haber et al. | 4,710,170 | 1987 |
| Butterfield | 4,713,056 | 1987 |
| Hesse | 4,731,068 | 1988 |

While each of the above-identified references is useful for its particular purpose, each still nonetheless has a number of drawbacks. For example, such syringes often employ locking arrangements that are often quite complicated requiring the use of numerous specialized parts all of which require specialized fabrication, which increases the cost thereof. Also, such syringes are often capable of being forced, or otherwise tampered with, so that the locking arrangement can be overcome, permitting the syringe to be recharged and reused.

Accordingly, it can be seen that there remains a need for a non-rechargeable, non-reusable hypodermic syringe for the delivery of a substance, which syringe is simple in construction, is comprised of a minimum number of elements and which is not capable of being forced, or otherwise tampered with, so that the locking arrangement thereof cannot be overcome and the syringe cannot be recharged or reused.

SUMMARY OF THE INVENTION

It is a primary object of the present invention to provide a non-rechargeable hypodermic syringe which can be loaded and utilized in a conventional manner.

It is another object of the present invention to provide such a non-rechargeable hypodermic syringe that is simple in construction and easy to fabricate, being made from a minimum number of elements.

It is still another object of the present invention to provide such a non-rechargeable hypodermic syringe that has a locking arrangement for the syringe that is not capable of being forced, overcome or otherwise tampered with, so that the syringe cannot be recharged or reused.

In accordance with the teachings of the present invention, a non-rechargeable syringe for use with a needle for the administration of medication and for immunization is disclosed that has a barrel, a retaining ring and a plunger. The barrel receives therein the substance to be delivered and has a forward end and a rearward end. The needle is carried on the forward end of the barrel for delivering the contents thereof The plunger includes a forward end and a rearward end that is remote therefrom The plunger is slidably disposed with the forward end thereof received in the barrel for sliding rearward movement towards a rearward position for aspirating the substance into the barrel. The plunger is also disposed for sliding forward movement towards a forward position In this manner, the contents of the barrel are forced through the forward end of the barrel and the needle carried thereon for the delivery of the contents of the barrel. The rearward end of the plunger is located outside of the barrel for being gripped, so as to effectuate the sliding movement of the plunger in the barrel. A retaining ring is circumferentially disposed near the rearward end of the barrel between the plunger and the barrel. The plunger has at least one notch formed therein between the first and second ends thereof. The barrel further has an internal inwardly-flared tab formed therein. This tab is oriented towards the forward end of the barrel. The tab is also inwardly biased. The retaining ring forces the tab outwardly such that during rearward movement of the plunger to aspirate substance into the barrel, the plunger may slide freely rearwardly. During forward movement of the plunger to deliver the substance, the retaining ring may move forwardly with the plunger permitting the tab to be inwardly biased. Also, during subsequent rearward movement of the plunger, the tab is received in the notch that is formed in the plunger under the inward biasing action. This prevents the plunger from further sliding rearwardly into a position wherein the syringe could be recharged for the further use thereof, so that the syringe is non-rechargeable.

In a preferred embodiment, means is provided that is formed between the retaining ring and the plunger for cooperating the forward movemen of the retaining ring with the movement of plunger.

These and other objects of the present invention will become apparent from a reading of the following specification, taken in conjunction with the enclosed drawings.

BRIEF DESCRIPTION OF THE DRAWINGS

FIGS. 2-7 illustrate, in cross-section, the use of the non-rechargeable syringe of the present invention for demonstrating the movement and co-action of the various elements thereof.

DESCRIPTION OF THE PREFERRED EMBODIMENT

Figure 1:
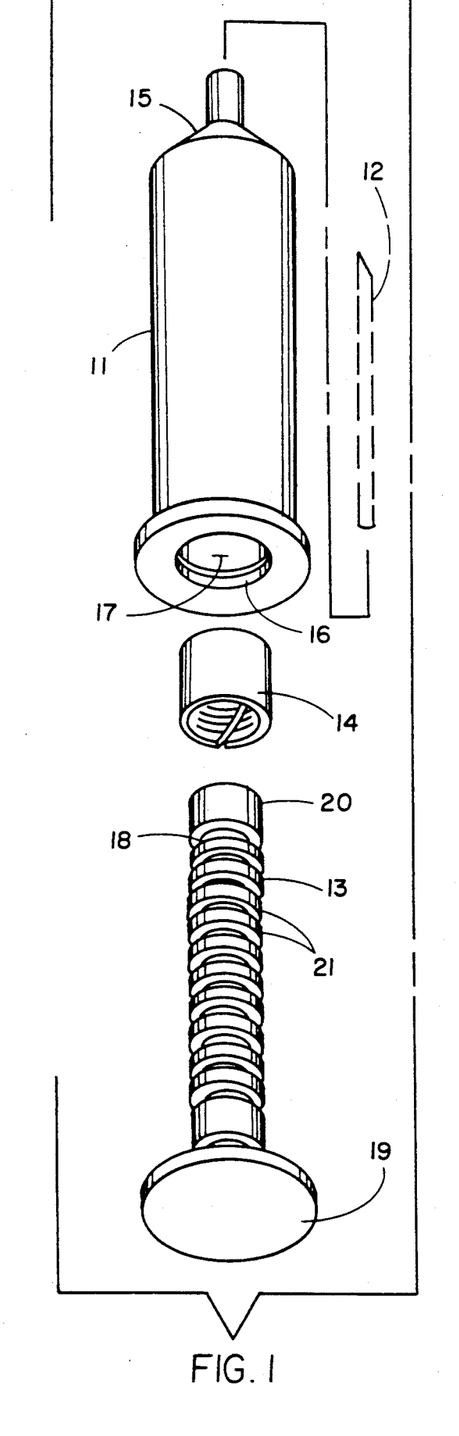
FIG. 1 is an exploded perspective view of the non-rechargeable syringe of the present invention with the barrel thereof partially removed therefrom for the sake of clarity.

Referring now to the drawings, the syringe 10 is seen in FIG. 1 to be comprised of a barrel 11, a plunger 13 and a retaining ring 14. A needle 12 is used with the syringe and may be integrally molded to the barrel 11, may be removable, or may be disposable. A needle of any size consistent with the size of the syringe may be used.

The barrel 11 is substantially hollow having a forward end 15 and a rearward end 16 that is remote therefrom. Both the forward and rearward ends 15 and 16, respectively, are open-ended. A longitudinal passageway 17 is formed through the barrel 11 extending from the forward end 15 to the rearward end 16 thereof. The substance to be delivered is received (drawn) in the passageway 17 for storage therein until the delivery thereof.

Carried on the forward end 15 of the barrel 11 is the needle 12. The needle 12 is in communication with the forward end 15 for permitting the substance to pass therethrough, to and from the forward end 15. In this manner, the substance may be drawn into or delivered from the syringe 10 via the needle 12, as desired The walls of the internal passageway 17 are substantially smooth, so as to permit the smooth sliding movement of the plunger 13 in the barrel 11. Preferably, the diameter of the internal passageway 17 (the internal diameter of the barrel) near the rearward end 16 is slightly smaller than the diameter of the remainder of the passageway.

Figure 2:
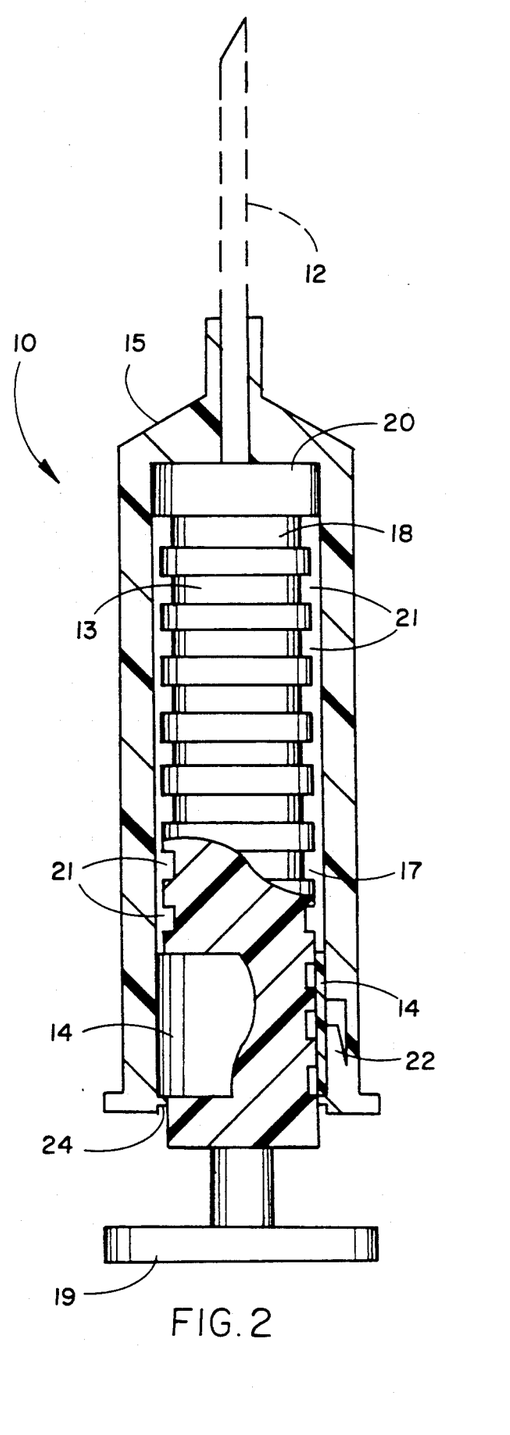
FIG. 2 is a cross-section view of the syringe, as it is obtained before the use thereof.

Referring to FIG. 2, the plunger 13 includes a forward end 18 and a rearward end 19 that is remote from the forward end 18. The forward end 18 of the plunger 13 includes a plunger head 20 that slidably engages the walls of the passageway 17 for either forcing the substance in the passageway 17 outwardly therefrom through the forward end 15 of the barrel 11 or for drawing the substance into the passageway 17 through the forward end 15. The plunger head 20 may have a means thereon for effecting a liquid seal between the forward end 18 and the passageway 18. This may be a gasket, O ring or any other means known to those skilled in the art.

Figure 4:
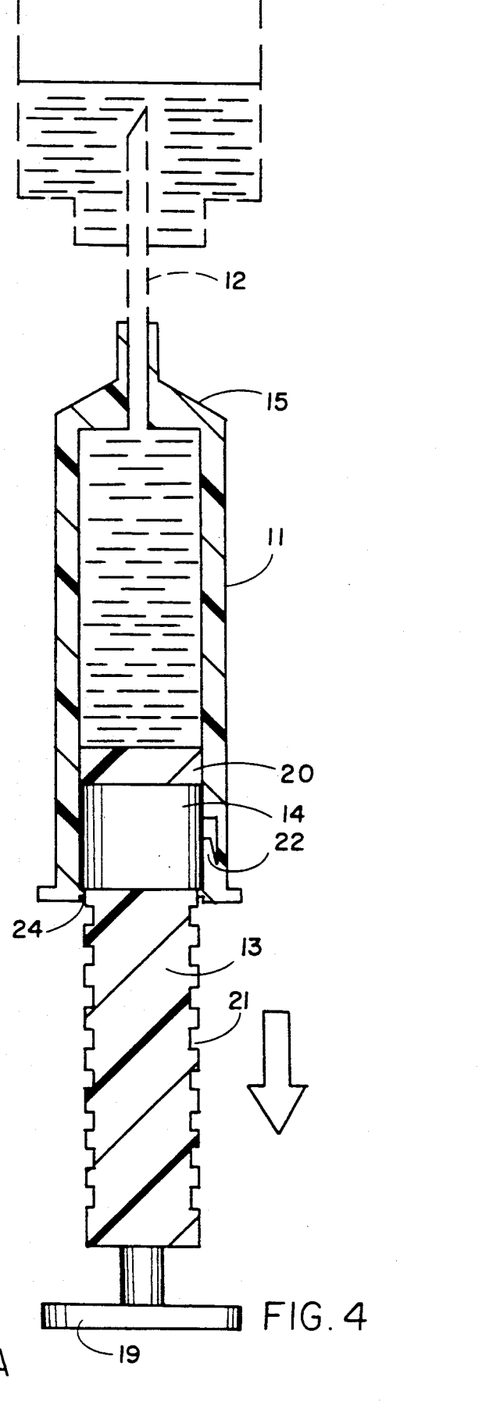
FIG. 4 is a cross-section view of the syringe with the components thereof in the rearward position wherein the syringe is fully charged with the substance to be delivered.
Figure 6:
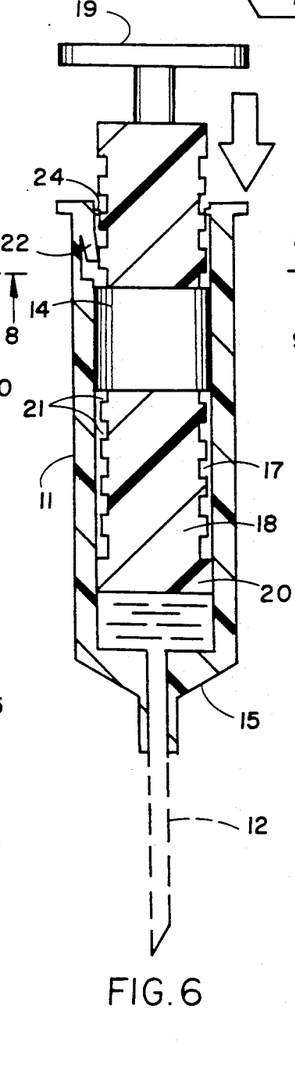
FIG. 6 is a cross-section view of the syringe with the components thereof in the forward position, wherein the syringe is near the forward end of the barrel after having delivered most of the substance and further showing the retaining ring (shown in plan view) having moved forwardly to permit the tab to be inwardly biased.

When slidably disposed in the barrel 11, the forward end 18 of the plunger 13 is received in the barrel 11 for sliding rearward movement towards a rearward position (FIG. 4) and for sliding forward movement towards a forward position (FIG. 6). In the forward position, the contents of the barrel 11 are forced through the forward end 15 thereof and the needle 12 carried thereon. In this manner, the contents of the barrel 11 are delivered for the use thereof. In the rearward position, the plunger 13 at least partially extends from the barrel 11. The syringe 10 is thus ready to deliver the contents of the barrel 11.

The rearward end 19 of the plunger 13 defines a gripping portion 19 by which the plunger 13 is gripped for effectuating the sliding movement thereof, as will be discussed.

At all times, the gripping portion 19 of the plunger 13 is situated outside of the barrel 11 for the gripping thereof.

With further reference now to the drawings, the unique locking mechanism that makes the syringe non-rechargeable is discussed.

The plunger 13 has at least one notch 21 formed therein between the forward and rearward ends 18 and 19, respectively, thereof. Preferably, the notch 21 is in the form of an annular notch formed about the external circumference of the plunger 13. It is further preferred that a plurality of such notches 21 are provided that are longitudinally spaced along the plunger 13.

The barrel 11 has at least one internal inwardly-flared (inclined) tab 22 formed in the passageway 17 thereof at substantially the rearward end 16 of the barrel 11. Preferably, a plurality of such tabs 22 are formed in the passageway 17 of the barrel 11 being circumferentially spaced about the passageway 17 of the barrel 11. It is further preferred that three such tabs 22 be provided, each being circumferentially spaced about the barrel 11 120° apart from one another, so as to annularly (circumferentially) surround the plunger 13.

Each of the tabs 22 is constantly inwardly resiliently-biased towards the plunger 13. The tabs 22 are oriented towards the forward end 15 of the barrel 11. During the forward movement of the plunger 13 towards the forward position, the plunger 13 rides over the tab(s) 22, and forces the tab(s) 22 outwardly against the inward biasing action. This arrangement permits the plunger 13 to be freely slid forwardly from the rearward position to the forward position.

In the above-described arrangement, during attempted rearward movement of the plunger of a "spent" syringe (as shall be more fully discussed below), the tab(s) 22 are received in the notch(es) 21 being forced outwardly under the inward biasing action. This positioning (seating) of the tab(s) 22 in the notch(es) 21 results in circumferential annular engagement and retention of the plunger 13, thereby preventing the plunger 13 from being further rearwardly slid towards or into a position wherein the syringe 10 could be recharged for the further use thereof. Thus, the syringe 10 provided is non-rechargeable.

In this respect, is it noted that the circumferential (annular) engagement provided by the use of several tabs 22 provides an increase in retaining strength and in the stability of the syringe 10.

The retaining ring 14 is circumferentially disposed in the passageway 17 between the plunger 13 and the barrel 11 for sliding forward movement towards the forward position. Preferably, the retaining ring 14 is a split ring which is expandable. The retaining ring 14 is disposed in the rear end of the passageway 17 where the diameter of the passageway 17 is smaller. The ring 14 also serves to keep the tabs 22 outwardly until the ring is moved forwardly in the passageway 17 when the plunger 13 is slid forwardly, as will be discussed.

Figure 3:
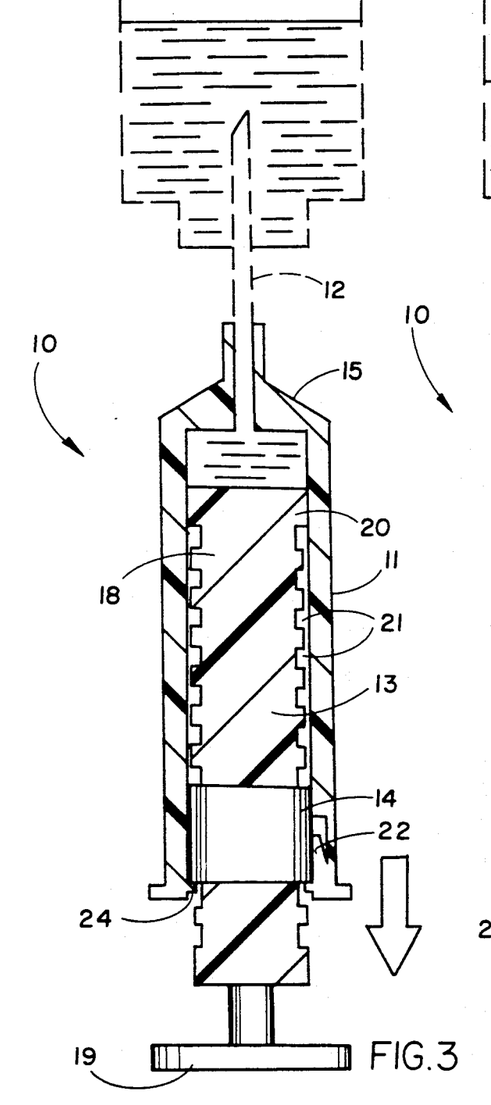
FIG. 3 is a cross-section view of the syringe with the plunger and the retaining ring being slidingly rearwardly moved towards the rearward position for drawing into the syringe, the substance to be delivered.
Figure 3A:
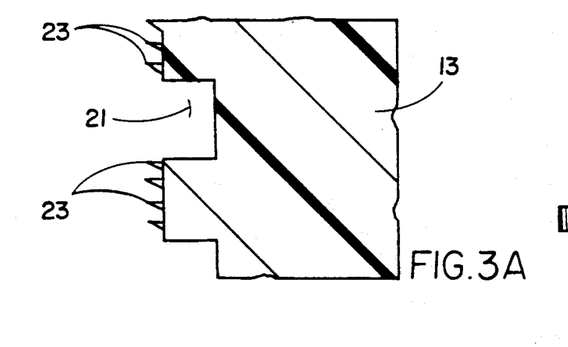
FIG. 3A is an enlarged cross-section view of a portion of the syringe showing the teeth on the plunger to engage the cooperating means on the retaining ring.

Means are formed between the retaining ring 14 and the plunger 13 for providing cooperating movement of the ring 14 and the plunger 13. Preferably, as shown in FIG. 3A, this means is provided by a plurality of ratchet teeth 23 formed on the plunger 13 (between the forward end 18 and the rearward end 19) and cooperating teeth 25 or notches on an inner wall of the retaining ring 14. Another alternative could be that the teeth 23 were formed on the retaining ring 14 to matingly engage serrations on the plunger 13. Alternatively, teeth 23 formed on the plunger 13 (between the forward end 18 and the rearward end 19) may matingly engage and cooperate with a serrated internal wall formed on the retaining ring 14. Still another alternative may be the frictional forces between the plunger 13 and the inner wall of the retaining ring 14. In this manner, sliding forward movement of the plunger 13 in the barrel 11 concomitantly slidingly moves the retaining ring 14 therewith.

Finally, it is noted that the rearward end 16 of the barrel 11 has means 24 defined therein between between the barrel and the passageway 17. This means provides a stop. This stop 24 prevents the retaining ring 14 from being moved rearwardly from the barrel 11 with the plunger 13 when rearwardly moving the plunger 13 into the rearward position for drawing the substance into the passageway 17 of the barrel 11. The stop 24 may be a shoulder on the barrel 11. Alternatively, the means is a ring stop having teeth or ridges which engage the rear end of the barrel 11 to secure the ring stop to the barrel 11 and to prevent the retaining ring 14 from being moved from the barrel 11. The ring stop is formed as an annular ring having an opening therein through which the plunger may be moved backwardly and forwardly.

Having thus described the structure of the non-rechargeable syringe 10 of the present invention, to better explain the syringe 10 and the advantageous features thereof, the operation of the syringe 10 is now described.

Figure 8:
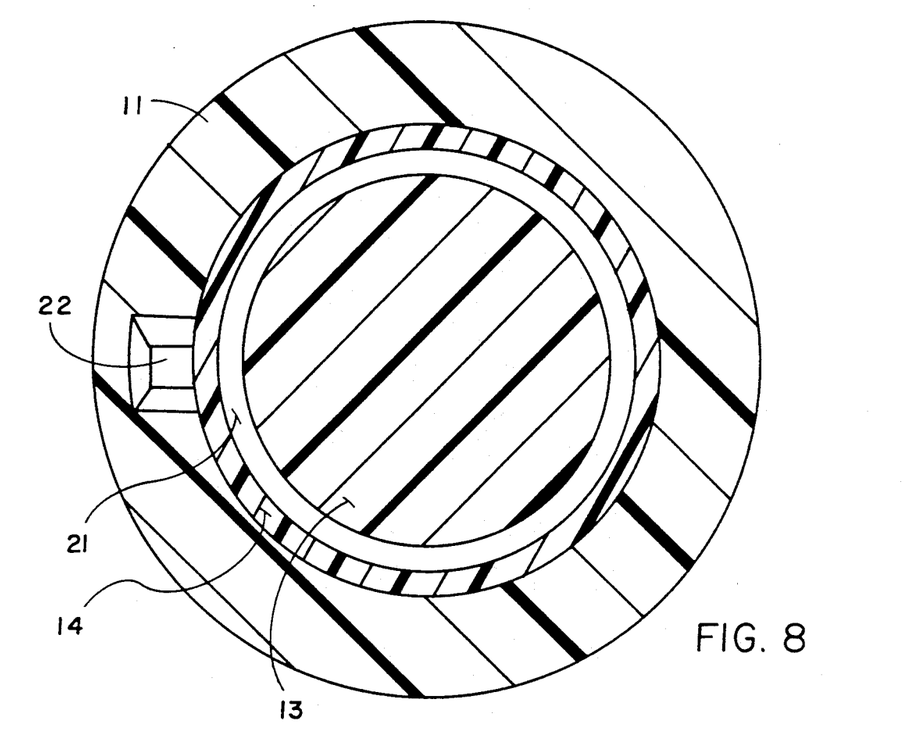
FIG. 8 is a cross-section view taken across the lines 8—8 of FIG. 5 and drawn to an enlarged scale to show the inter-relationship of the tab, the retaining ring and the plunger when the syringe is about to deliver the substance in the syringe.
Figure 10A:
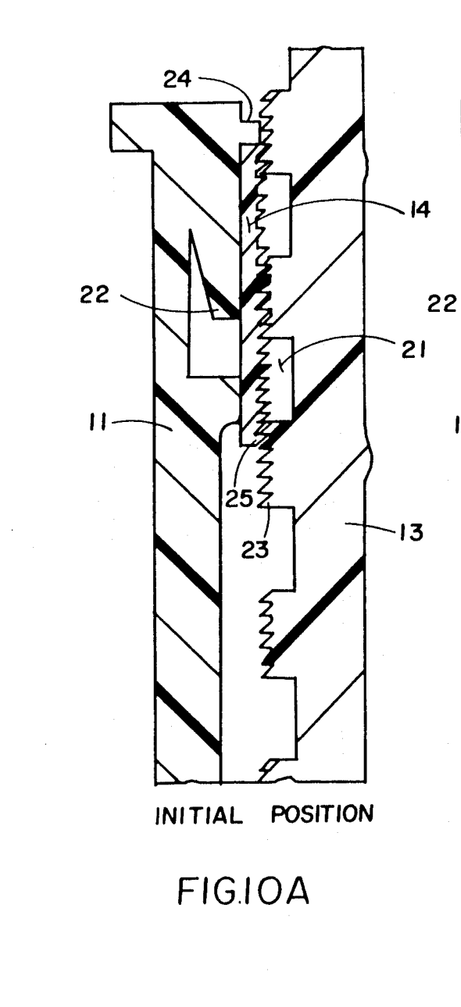
FIGS. 10A-10E illustrate in cross section, enlarged scale views of the movement of the sliding ring relative to the plunger and to the tab or barrel to demonstrate the interaction of these elements as follows: initially, during the loading of the syringe, during injecting with the syringe, the final position and the non-rechargeable feature.

When received, the syringe 10 is in its first forward position with the plunger 13 fully disposed in the barrel 11 (with the gripping portion 19 extending therefrom) (FIG. 2). The retaining ring 14 is at the rearward end 16 of the barrel 11, with the cooperating means between the plunger 13 and the retaining ring 14. In this position, the retaining ring 14 covers the uppermost notch 21 and extends over the tab(s) 22, pushing the tab(s) 22 outwardly against its natural resilient-biasing action (FIG. 8). The retaining ring 14 further abuts against the shoulder 24 (stop) defined in the barrel 11 at the rearward end 16 thereof (FIG. 10A).

Figure 10B:
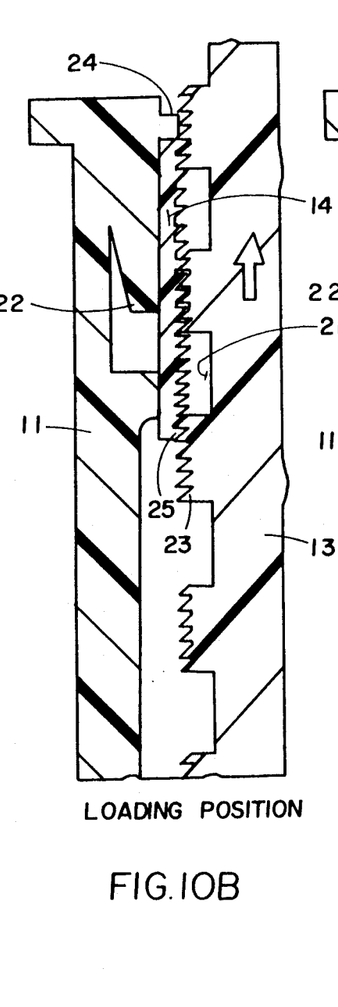

With the tab(s) 22 so covered and retained outwardly by the retaining ring 14, the plunger 13 may be pulled by use of the grip 19 in a rearward direction into the rearward position. The cooperating ratchet teeth 23 ride over the teeth 25 on retaining ring 14, which is held in place by the stop 24. Thus, (FIGS. 3 and 4) the substance to be delivered can be drawn or aspirated into the passageway 17 in the barrel 11 through the needle 12 and the forward end 15 of the barrel 11 by the suction in the passageway 17 created by the sliding rearward movement of the plunger 13 (FIG. 10B).

Figure 5:
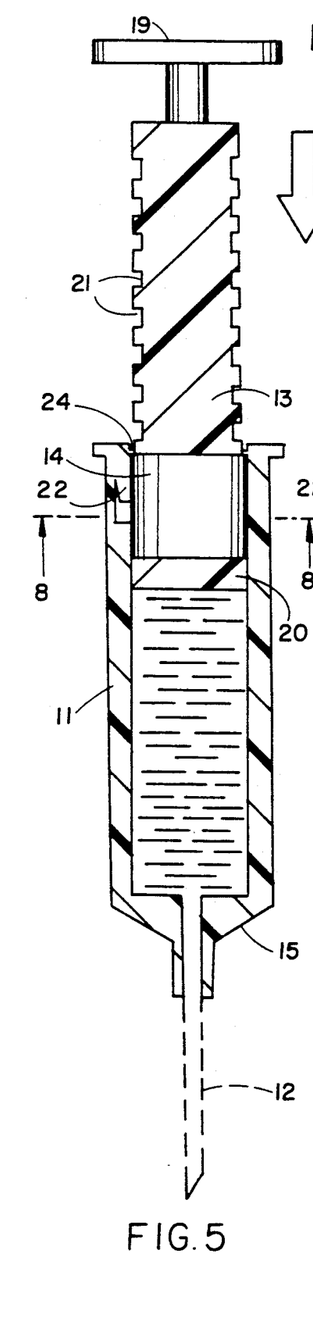
FIG. 5 is a cross-section view of the syringe with the plunger and the retaining ring (shown in plan view) being slidingly forwardly moved towards the forward position for delivering the substance from the syringe during use thereof.
Figure 10C:
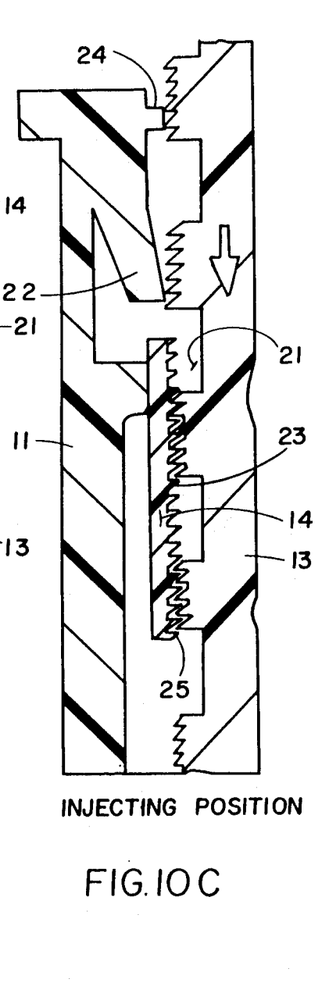

To deliver the substance (contents) of the barrel 11 of the syringe 10, (FIG. 5) the plunger 13 may be pushed, by the use of the grip 19, in the forward movement into the forward position. The means of cooperation (the teeth 23, 25) between the plunger 13 and the retaining ring 14 moves the ring 14 forwardly concomitantly with the forward movement of the plunger 13. The ring 14 moves until the ring 14 is disposed in the slightly larger diameter portion of the passageway 17. The split ring 14 expands to accommodate the larger diameter. The increase in diameter is approximately equal to the size of the teeth 23 on the ring 14. The ring 14 may not slide the entire length of the passageway 17. In this fashion, the substance is delivered for use via the forward end 15 of the barrel 11 and the needle 12 (FIG. 10C).

Figure 7:
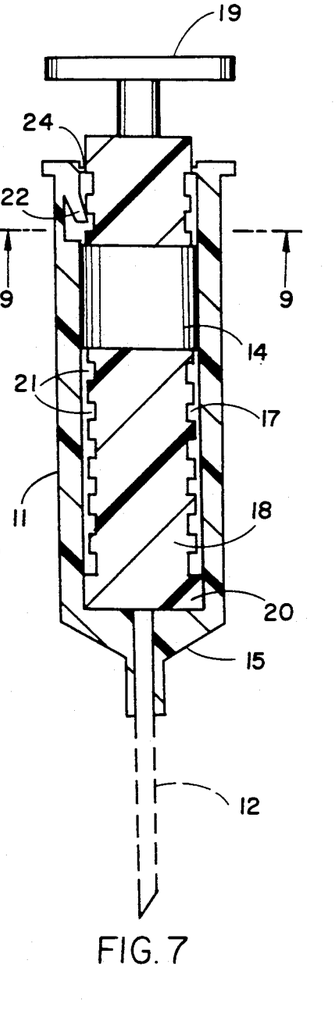
FIG. 7 is a cross-section view showing how the components interact to prevent the recharging of the syringe after the use thereof, when one tries to rearwardly move the plunger.
Figure 9:
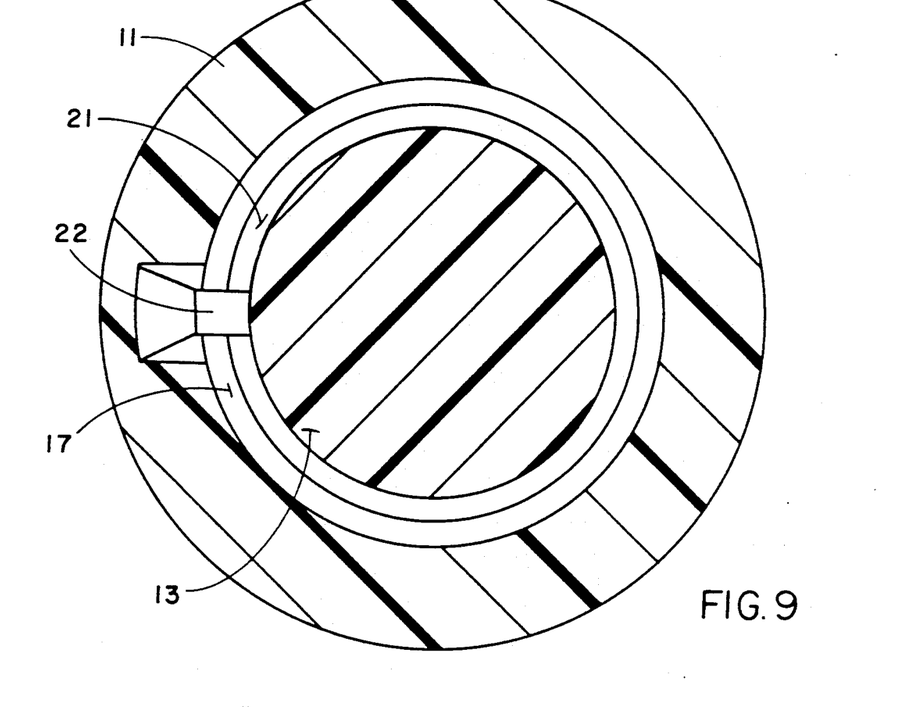
FIG. 9 is a cross-section view taken across the lines 9—9 of FIG. 7 and drawn to an enlarged scale to show the tab engaging the plunger to prevent recharging of the syringe.
Figure 10D:
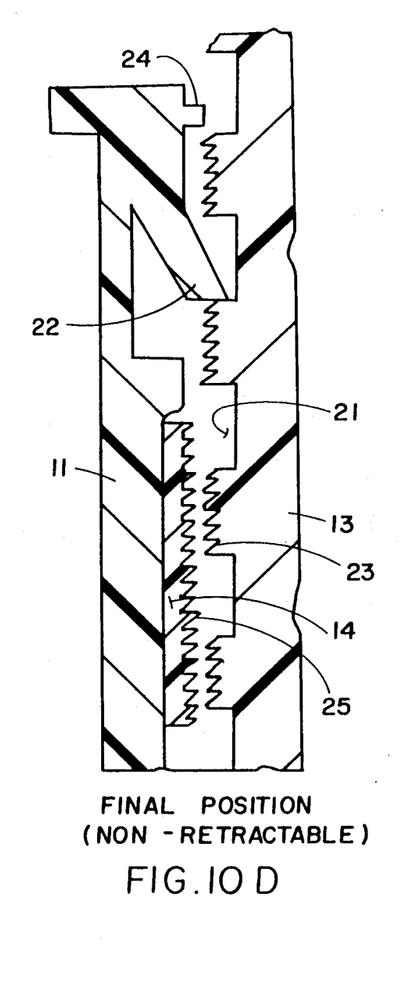

During this concomitant forward movement of the retaining ring 14 and the plunger 13, when the retaining ring 14 has moved forwardly and out of contact with the tab(s) 22, the tab(s) 22 spring inwardly (FIG. 6). When an attempt is made to move the plunger 13 rearwardly, the rearward end of the tab(s) 22 abut the ring 14, holding it in place. Referring to FIGS. 7 and 9, further rearward movement results in the tab(s) 22 circumferentially (annularly) engaging the notch 21, preventing further rearward movement of the plunger 13 towards the rearward position. In this respect, it is preferred to form the uppermost notch(es) 21 as close to the rearward end 19 as possible while still being located in the barrel 11 when the plunger 1 is in the forward position (FIG. 10D). Further, since the plunger 13 has a plurality of notches 21 extending substantially the length of the plunger 13, any rearward movement of the plunger 13 is prevented even if the plunger 13 has not been moved to a full forward position (as for example when the syringe has not been fully charged with the substance to be delivered).

Figure 10E:
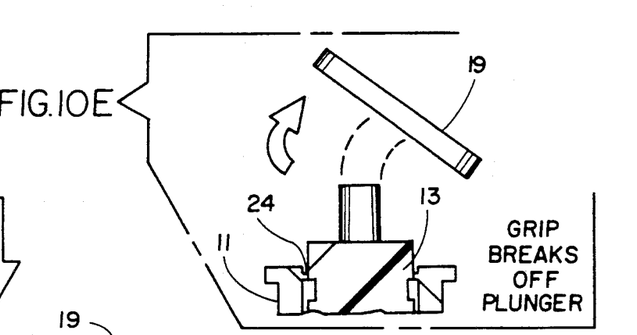

Should one try to further pull the plunger 13, then the plunger grip 19 is formed so that the grip 19 snaps off the plunger 13. In this respect, it is preferable that the grip 19 be frangibly carried on the rearward end of the plunger 13. To achieve this, the grip 19 must be attached to the remainder of the plunger 13 securely enough to prevent it from pulling loose when the plunger 13 is rearwardly moved into the rearward position to draw into the syringe 10 the substance to be delivered. On the other hand, the nexus must break at a force that is considerably less than the force required to pull the plunger 13 from the barrel 11 against the annular engagement action of the tab(s) 22 in the notch(es) 21 (FIG. 10E).

Obviously, many modifications may be made without departing from the basic spirit of the present invention. Accordingly, it will be appreciated by those skilled in the art that within the scope of the appended claims the invention may be practiced other than has been specifically described herein.

What is claimed is:

1. A non-rechargeable syringe for use with a needle comprised of:
   a barrel for receiving therein a substance to be delivered, the barrel having a forward end and a rearward end remote therefrom;
   the needle carried on the forward end of the barrel for delivering the contents of the barrel;
   a plunger including a forward end and a rearward end remote therefrom, the plunger being slidably disposed with the forward end thereof received in the barrel for sliding rearward movement towards a rearward position for aspirating the substance into the barrel and further for sliding forward movement towards a forward position, whereby the contents of the barrel are forced through the forward end of the barrel and through the needle carried thereon for delivery of the contents of the barrel, the rearward end of the plunger being located outside of the barrel for being gripped so as to effectuate the sliding movement of the plunger in the barrel;
   a retaining ring circumferentially disposed near the rearward end of the barrel between the plunger and the barrel;
   means formed between the retaining ring and the plunger for cooperating the forward movement of the retaining ring with the movement of the plunger;
   the plunger having at least oen notch formed therein between the first and second ends thereof; and
   the barrel further having an inernal inwardly-flared tab formed therein oriented towards the forward end of the barrel, the tab being inwardly-biased, the retaining ring forcing the tab outwardly such that during rearward movement of the plunger to aspirate the substance into the barrel, the plunger may slide freely rearwardly, during forward movement of the plunger to deliver the substance, the retaining ring may move forwardly with the plunger permitting the tab to be inwardly biased and further such that during subsequent rearward movement of the plunger, the inwardly biased tab is received in the notch formed in the plunger, thereby preventing the plunger from being further slid rearward into a position wherein the syringe could be recharged for the further use thereof, so that the syringe is non rechargeable.

2. The non-rechargeable syringe of claim 1, further comprised of:
   the retaining ring having a serrated internal wall; and
   a plurality of ratchet teeth formed on the plunger between the first and second ends thereof for matingly engaging and cooperating with the serrated internal wall, such that the sliding forward movement of the plunger in the barrel concomitantly slidingly forwardly moves the retaining ring therewith.

3. The non-rechargeable syringe of claim 1, wherein the retaining ring is a split ring such that the ring may be expandable and contractable.

4. The non-rechargeable syringe of claim 3 wherein the rearward end of the barrel has a first internal diameter and the forward end of the barrel has a second internal diameter, the second diameter being larger than the first diameter such that when the retaining ring moves forwardly concomitantly with forward movement of the plunger, the retaining ring may expand to the second diameter such that the retaining ring is prevented from forcing the tab outwardly and such that the tab may be received in the notch in the plunger to prevent subsequent rearward movement of the plunger.

5. The non-rechargeable syringe of claim 1, further comprised of:
   the rearward end of the barrel having means thereon to provide a stop for the retaining ring.

6. The non-rechargeable syringe of claim 1, wherein the notch formed in the plunger is an annular notch.

7. The non-rechargeable syringe of claim 6, wherein the barrel has a plurality of inwardly-flared tabs formed therein, each of said tabs being circumferentially spaced about the barrel for being received in the annular notch for circumferential engagement and retention of the plunger.

8. The non-rechargeable syringe of claim 7, wherein three inwardly-flared tabs are formed in the barrel, each of said tabs being circumferentially spaced about the barrel 120° apart from one another for being received in the annular notch for circumferential engagement and retention of the plunger.

9. The non-rechargeable syringe of claim 1, wherein the plunger has a plurality annular notches formed therein, said notches being longitudinally spaced along the plunger.

10. The non-rechargeable syringe of claim 1, further comprised of:
    a plurality of cooperating ratchet teeth formed on the plunger between the first and second ends thereof and on the retaining ring, such that the sliding movement of the plunger in the barrel concomitantly slidingly forwardly moves the retaining ring therewith.

11. The non-rechargeable syringe of claim 1, further comprised of:
    a plunger grip being frangibly carried on the rearward end of the plunger, such that when the tabs are engaged in the notch of the plunger, further pulling of the plunger towards the rearward position results in the plunger grip snapping off of the plunger.

12. A non-rechargeable syringe for use with a needle comprised of:
    a barrel for receiving therein a substance to be delivered, the barrel having a forward end and a rearward end remote therefrom;
    the needle carried on the forward end of the barrel for delivering the contents of the barrel;
    a plunger including a forward end and a rearward end remote therefrom, the plunger being slidably disposed with the forward end thereof received in the barrel for sliding rearward movement towards a rearward position for aspirating the substance into the barrel and further for sliding forward movement towards a forward position, whereby the contents of the barrel are forced through the forward end of the barrel and the needle carried thereon for the delivery of the contents of the barrel, the rearward end of the plunger being located outside of the barrel for being gripped so as to effectuate the sliding movement of the plunger in the barrel;

a retaining ring circumferentially disposed near the rearward end of the barrel between the plunger and the barrel;

means formed between the retaining ring and the plunger for cooperating the forward movement of the retaining ring with the movement of the plunger;

the rearward end of the barrel having means thereon to provide a stop for the retaining ring;

the plunger having at least one annular notch formed therein between the first and second ends thereof; and the barrel further having an internal inwardly-flared tabs formed therein oriented towards the forward end of the barrel, the tab being inwardly-biased, the retaining ring forcing the tab outwardly such that during rearward movement of the plunger to aspirate the substance into the barrel, the plunger may slide freely rearwardly, during forward movement of the plunger to deliver the substance , the retaining ring may move forwardly with the plunger permitting the tab to be inwardly biased and further such that during subsequent rearward movement of the plunger, the inwardly biased tab is received in the notch formed in the plunger, thereby preventing the plunger from being further slid rearward into a position wherein the syringe could be recharged for the further use thereof, so that the syringe is non rechargeable.

13. The non-rechargeable syringe of claim 12, wherein the plunger has a plurality of annular notches formed therein, said notches being longitudinally spaced along the plunger.

14. The non-rechargeable syringe of claim 12, further comprised of:

a plunger grip being frangibly carried on the rearward end of the plunger, such that when the tabs are engaged in the notch of the plunger further pulling of the plunger towards the rearward position results in the plunger grip snapping off the plunger.

15. The non-rechargeable syringe of claim 12, wherein the retaining ring is a split ring such that the ring may be expandable and contractable.

16. The non-rechargeable syringe of claim 15 wherein the rearward end of the barrel has a first internal diameter and the forward end of the barrel has a second internal diameter, the second diameter being larger than the first diameter such that when the retaining ring moves forwardly concomitantly with forward movement of the plunger, the retaining ring may expand to the second diameter such that the retaining ring is prevented from forcing the tab outwardly and such that the tab may be received in the notch in the plunger to prevent subsequent rearward movement of the plunger.

17. A non-rechargeable syringe for use with a needle comprised of:

a barrel for receiving therein a substance to be delivered, the barrel having a forward end and a rearward end remote therefrom;

the needle carried on the forward end of the barrel for delivering the contents of the barrel;

a plunger including a forward end and a rearward end remote therefrom, the plunger being slidably disposed with the forward end thereof received in the barrel for sliding rearward movement towards a rearward position for aspirating the substance into the barrel and further for sliding forward movement towards a forward position, whereby the contents of the barrel are forced through the forward end of the barrel and the needle carried thereon for the delivery of the contents of the barrel, the rearward end of the plunger being located outside of the barrel for being gripped so as to effectuate the sliding movement of the plunger in the barrel;

a retaining ring circumferentially disposed near the rearward end of the barrel between the plunger and the barrel;

means formed between the retaining ring and the plunger for cooperating the forward movement of the retaining ring with the movement of the plunger;

the rearward end of the barrel having means thereon to provide a stop for the retaining ring;

the plunger having at least one annular notch formed therein between the first and second ends thereof; and the barrel further having an internal inwardly-flared tabs formed therein oriented towards the forward end of the barrel, the tabs being inwardly-biased, the retaining ring forcing the tabs outwardly such that during rearward movement of the plunger to aspirate the substance into the barrel, the plunger may slide freely rearwardly, during forward movement of the plunger to deliver the substance , the retaining ring may move forwardly with the plunger permitting the tabs to be inwardly biased and further such that during subsequent rearward movement of the plunger, the inwardly biased tabs are received in the notch formed in the plunger, thereby preventing the plunger from being further slid rearward into a position wherein the syringe could be recharged for the further use thereof, so that the syringe is non rechargeable.

18. The non-rechargeable syringe of cliam 17, wherein the retaining ring is a split ring such that the ring may be expanded and contractable.

19. The non-rechargeable syringe of claim 18 wherein the rearward end of the barrel has a first internal diameter and the forward end of the barrel has a second internal diameter, the second diameter being larger than the first diameter such that when the retaining ring moves forwardly concomitantly with forward movement of the plunger, the retaining ring may expand to the second diameter such that the retaining ring is prevented from forcing the tab outwardly and such that the tab may be received in the notch in the plunger to prevent subsequent rearward movement of the plunger.

20. A non-rechargeable syringe for use with a needle comprised of:

a barrel for receiving therein a substance to be delivered, the barrel having a forward end and a rearward end remote therefrom;

the needle carried on the forward end of the barrel for delivering the contents of the barrel;

a plunger including a forward end and a rearward end remote therefrom, the plunger being slidably disposed with the forward end thereof received in the barrel for sliding rearward movement towards a rearward position for aspirating the substance into the barrel and further for sliding forward movement towards a forward position, whereby the contents of the barrel are forced through the forward end of the barrel and the needle carried thereon for the delivery of the contents of the barrel, the rearward end of the plunger being located outside of the barrel for being gripped so as to effectuate the sliding movement of the plunger in the barrel;

a retaining ring circumferentially disposed in the barrel between the plunger and the barrel for sliding forward movement towards the forward position and for sliding rearward movement towards the rearward position, the retaining ring having a serrated internal wall;

a plurality of ratchet teeth formed on the plunger between the first and second ends thereof for matingly engaging and cooperating with the serrated internal wall, such that the sliding forward movement of the plunger in the barrel concomitantly slidingly forwardly moves the retaining ring therewith;

the rearward end of the barrel having a means thereon to provide a stop for the retaining ring;

the plunger having at least one annular notch formed therein between the first and second ends thereof; and the barrel further having an internal inwardly-flared tab formed therein oriented towards the forward end of the barrel, the tab being inwardly-biased, the retaining ring forcing the tab outwardly such that during rearward movement of the plunger to aspirate the substance into the barrel, the plunger may slide freely rearwardly during forward movement of the plunger permitting the tab to be inwardly biased and further such that during subsequent rearward movement of the plunger, the inwardly biased tab is received in the notch formed in the plunger, thereby preventing the plunger from being further slid rearward into a position wherein the syringe could be recharged for the further use thereof, so that the syringe is non-rechargeable.

21. The non-rechargeable syringe of claim 20, wherein the plunger has a plurality annular notches formed therein, said notches being longitudinally spaced along the plunger.

22. The non-rechargeable syringe of claim 20, further comprised of:
a plunger grip being frangibly carried on the rearward end of the plunger, such that when the tabs are engaged in the notch of the plunger, further pulling of the plunger towards the rearward position results in the plunger grip snapping off the plunger.

23. A non-rechargeable syringe for use with a needle comprised of:
a barrel for receiving therein a substance to be delivered, the barrel having a forward end and a rearward end remote therefrom;
the needle carried on the forward end of the barrel for delivering the contents of the barrel;
a plunger including a forward end and a rearward end remote therefrom, the plunger being slidably disposed with the forward end thereof received in the barrel for sliding rearward movement towards a rearward position for aspirating the substance into the barrel and further for sliding forward movement towards a forward position, whereby the contents of the barrel are forced through the forward end of the barrel and the needle carried thereon for the delivery of the contents of the barrel, the rearward end of the plunger being located outside of the barrel for being gripped so as to effectuate the sliding movement of the plunger in the barrel;
a retaining ring circumferentially disposed in the barrel between the plunger and the barrel;
means formed between the retaining ring and the plunger for cooperating the forward movement of the retaining ring with the movement of the plunger;
the rearward end of the barrel having means thereon to provide a stop for the retaining ring;
the plunger having at least one annular notch formed therein between the first and second ends thereof; and
the barrel further having a plurality of internal inwardly-flared tabs formed therein oriented towards the forward end of the barrel, the tabs being inwardly-biased, the retaining ring forcing the tabs outwardly such that during rearward movement of the plunger to aspirate the substance into the barrel, the plunger may slide freely rearwardly, during forward movement of the plunger to deliver the substance, the retaining ring may move forwardly with the plunger permitting the tabs to be inwardly biased and further such that during subsequent rearward movement of the plunger, the inwardly biased tabs are received in the notch formed in the plunger, thereby preventing the plunger from being further slid rearward into a position wherein the syringe could be recharged for the further us thereof, so that the syringe is non rechargeable.

24. The non-rechargeable syringe of claim 23, wherein the plunger has a plurality annular notches formed therein, said notches being longitudinally spaced along the plunger.

25. The non-rechargeable syringe of claim 23, further comprised of:
a plunger grip being frangibly carried on the rearward end of the plunger, such that when the tabs are engaged in the notch of the plunger further pulling of the plunger towards the rearward position results in the plunger grip snapping off the plunger.

26. The non-rechargeable syringe of claim 23 wherein the retaining ring is a split ring such that the ring may be expandable and contractable.

27. The non-rechargeable syringe of claim 24 wherein the rearward end of the barrel has a first internal diameter and the forward end of the barrel has a second internal diameter, the second internal diameter being larger than the first diameter such that when the retaining ring moves forwardly concomitantly with forward movement of the plunger, the retaining ring may expand to the second diameter such that the retaining ring is prevented from forcing the tab outwardly and such that the tab may be received in the notch in the plunger to prevent subsequent rearward movement of the plunger.

28. A non-rechargeable disposable hypodermic syringe for use with a needle, comprised of:
a barrel for receiving a substance therein;

the needle disposed on the barrel for aspirating the substance into the barrel and for delivering the substance from the barrel;

a plunger having a forward end slidably disposed in the barrel for sliding movement in a rearward direction for aspirating the substance into the barrel and in a forward direction for delivering the substance from the barrel, the plunger further having a rearward end extending from the barrel for gripping of the plunger to effectuate the sliding movement thereof in the barrel;

the plunger having at least one notch formed therein;

the barrel having at least one internal inwardly-flared tab formed therein being oriented towards the needle, the tab being resiliently inwardly-biased, a retaining ring slidably disposed in the barrel between the plunger and the barrel, so as to annularly surround at least a portion of the plunger;

a plurality of cooperating ratchet teeth formed between th retaining ring and the plunger, such that sliding of the plunger in the forward direction concomitantly slides the retaining ring therewith;

the retaining ring being initially-disposed between the tab of the barrel and the notch of the plunger forcing and retaining the tab outwardly against the biasing action of the tab, so that prior to any previous use of the syringe, the plunger may be slid in the rearward direction for aspirating the substance into the barrel, and such that during movement of the plunger in a forward direction to deliver the substance in the barrel, the retaining ring moves forwardly permitting the tab to be inwardly biased, and further such that during subsequent movement of the plunger in the rearward direction, the tab is biased into the notch formed in the plunger, thereby preventing the plunger from being further slid in the rearward direction, such that the syringe can not be recharged for reuse.

29. The non rechargeable syringe of claim 28 wherein the retaining ring is a split ring such that the ring may be expandable and contractable.

30. The non-rechargeable syringe of claim 29 wherein the rearward end of the barrel has a first internal diameter and the forward end of the barrel has a second internal diameter, the second diameter being larger than the first diameter such that when the retaining ring moves forwardly concomitantly with forward movement of the plunger, the retaining ring may expand to the first diameter such that the retaining ring is prevented from forcing the tab outwardly and such that the tab may be received in the notch in the plunger to prevent subsequent rearward movement of the plunger.

* * * * *

UNITED STATES PATENT AND TRADEMARK OFFICE
CERTIFICATE OF CORRECTION

PATENT NO. : 5,059,181
DATED : October 22, 1991
INVENTOR(S) : AGRAN

It is certified that error appears in the above-identified patent and that said Letters Patent is hereby corrected as shown below:

Column 2, line 12, after "thereof" and before "The", insert a period --.--;
Column 2, line 14, between "therefrom" and "The", insert a period --.--;
Column 2, line 19, between "position" and "In", insert a period --.--;
Column 2, line 47, change "movemen" to --movement--;
Column 3, line 66, after "desired" and before "The" in line 67, insert a period --.--;
Column 6, line 49, change "1" to --13--;
Column 7, line 38, change "oen" to --one--;
Column 7, line 40, change "inernal" to --internal--;
Column 9, line 19, change "tabs" to --tab--;

Column 10, line 27, change "an" to --a plurality of--;
Column 12, line 37, change "us" to --use--; and
Column 13, line 20, change "th" to --the--.

Signed and Sealed this

Third Day of August, 1993

Attest:

MICHAEL K. KIRK

Attesting Officer          Acting Commissioner of Patents and Trademarks